(12) United States Patent
Hirai

(10) Patent No.: US 8,379,084 B2
(45) Date of Patent: Feb. 19, 2013

(54) IMAGE PICKUP

(75) Inventor: Hideaki Hirai, Yokohama (JP)

(73) Assignee: Ricoh Company, Limited, Tokyo (JP)

( * ) Notice: Subject to any disclaimer, the term of this patent is extended or adjusted under 35 U.S.C. 154(b) by 445 days.

(21) Appl. No.: 12/486,246

(22) Filed: Jun. 17, 2009

(65) Prior Publication Data

US 2009/0316025 A1     Dec. 24, 2009

(30) Foreign Application Priority Data

Jun. 18, 2008 (JP) .................... 2008-159051
Jan. 23, 2009 (JP) .................... 2009-013235

(51) Int. Cl.
*H04N 7/18* (2006.01)
(52) U.S. Cl. ................ 348/143; 348/77; 348/78
(58) Field of Classification Search .......... 348/148, 348/151, 78, 77, 143, 117, 118
See application file for complete search history.

(56) References Cited

U.S. PATENT DOCUMENTS

| | | | |
|---|---|---|---|
| 5,555,464 A | | 9/1996 | Hatlestad |
| 6,151,065 A * | | 11/2000 | Steed et al. ............. 348/148 |
| 6,213,625 B1 * | | 4/2001 | Leadford et al. ......... 362/331 |
| 6,703,925 B2 * | | 3/2004 | Steffel .................. 340/425.5 |
| 7,221,363 B2 * | | 5/2007 | Roberts et al. ........... 345/204 |
| 7,755,016 B2 * | | 7/2010 | Toda et al. .............. 250/208.1 |
| 2002/0118282 A1 * | | 8/2002 | Nakamura ............... 348/148 |
| 2003/0058357 A1 * | | 3/2003 | Aotsuka ................. 348/272 |
| 2003/0214733 A1 * | | 11/2003 | Fujikawa et al. ......... 359/838 |
| 2004/0202001 A1 * | | 10/2004 | Roberts et al. ........... 362/494 |
| 2004/0256561 A1 | | 12/2004 | Beuhler et al. |
| 2005/0134699 A1 * | | 6/2005 | Nagashima et al. ....... 348/218.1 |

(Continued)

FOREIGN PATENT DOCUMENTS

CN     1568895 A     1/2005
CN     1680779 A     10/2005

(Continued)

OTHER PUBLICATIONS

Yasuhiro Satoh, et al., "High Accuracy Microlens Fabrication Method and it's Application to LD Beam Profile Converter" Ricoh Technical Report, No. 29, Dec. 2003, pp. 13-20. (With English Abstract).

(Continued)

*Primary Examiner* — Sinh Tran
*Assistant Examiner* — Selam Gebriel
(74) *Attorney, Agent, or Firm* — Oblon, Spivak, McClelland, Maier & Neustadt, L.L.P.

(57) ABSTRACT

An image pickup including a light emission portion that irradiates an object with near infrared; and an image pickup portion that receives a reflection light image of the object by the near infrared. The image pickup portion includes a lens array containing a substrate on which multiple lenses to respectively receive the reflection light image of the object by the near infrared are arranged; a light shield spacer that shields beams of light that have passed through the lens array from each other; a color filter separated into areas according to beams of light that pass through the light shield spacer, each of which transmits only particular beams of near infrared depending on the wavelengths thereof; and an image pickup element that simultaneously obtains multiple images of the object which are formed of each of the particular beams of near infrared having independent wavelengths that have passed through each of the areas of the color filter.

17 Claims, 8 Drawing Sheets

U.S. PATENT DOCUMENTS

| | | | |
|---|---|---|---|
| 2006/0034537 A1 | 2/2006 | Masaki | |
| 2006/0054780 A1 | 3/2006 | Garrood et al. | |
| 2006/0055800 A1 | 3/2006 | Ackland et al. | |
| 2006/0097172 A1 | 5/2006 | Park | |
| 2006/0104488 A1 | 5/2006 | Bazakos et al. | |
| 2007/0052805 A1 | 3/2007 | Inagaki et al. | |
| 2007/0221826 A1* | 9/2007 | Bechtel et al. | 250/208.1 |
| 2007/0296840 A1 | 12/2007 | Takada et al. | |
| 2008/0030596 A1* | 2/2008 | Sung et al. | 348/224.1 |
| 2008/0042227 A1* | 2/2008 | Asano et al. | 257/432 |
| 2008/0158359 A1* | 7/2008 | Takeda | 348/148 |
| 2008/0259191 A1* | 10/2008 | Imamura et al. | 348/294 |
| 2010/0157091 A1* | 6/2010 | Honda et al. | 348/223.1 |
| 2010/0231770 A1* | 9/2010 | Honda et al. | 348/308 |

FOREIGN PATENT DOCUMENTS

| | | |
|---|---|---|
| CN | 1830389 A | 9/2006 |
| EP | 1 010 997 A1 | 6/2000 |
| JP | 3325825 | 7/2002 |
| JP | 3397758 | 2/2003 |
| JP | 2004-191893 | 7/2004 |
| JP | 2006-71741 | 3/2006 |
| JP | 2006-246193 | 9/2006 |
| JP | 2007-4155 | 1/2007 |
| JP | 2007-41555 | 2/2007 |
| JP | 2007-74079 | 3/2007 |
| WO | WO 01/71811 A1 | 9/2001 |

OTHER PUBLICATIONS

Masayasu Ezaki, et al., "Development on human-sensitive sensor by Near Infrared Multi-band" Softpia Japan Collaborative Research Report, vol. 11, 2007, 12 pages. (With Partial English Translation).

Shin Yamamoto, et al., "Technologies on Built-in Sensor and Camera for Car" Technical Information Institute Co., Ltd., Oct. 31, 2005, 21 pages. (With Partial English Translation).

U.S. Appl. No. 12/485,315, filed Jun. 16, 2009, Hirai.

Office Action issued Oct. 26, 2011, in Chinese Patent Application No. 200910145890.4.

Office Action issued Jun. 30, 2011 in Chinese Patent Application No. 200910145890.4.

Search Report issued Jul. 20, 2011 in European Patent Application No. 09251563.4-1241/2136550.

Office Action mailed Dec. 9, 2010, in Chinese Patent Application No. 200910145890.4.

* cited by examiner

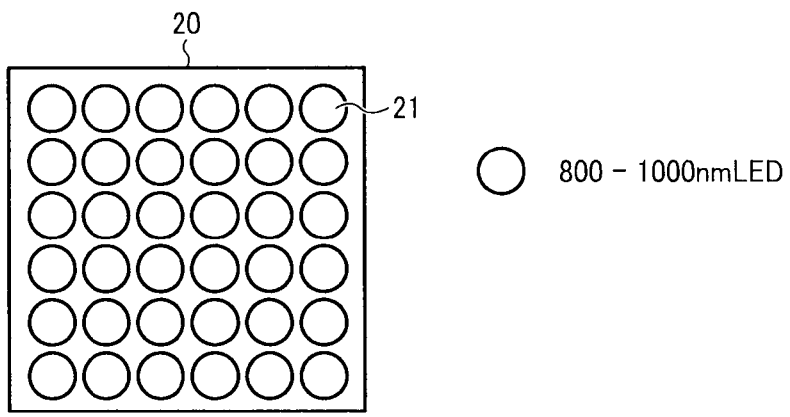
FIG. 3A
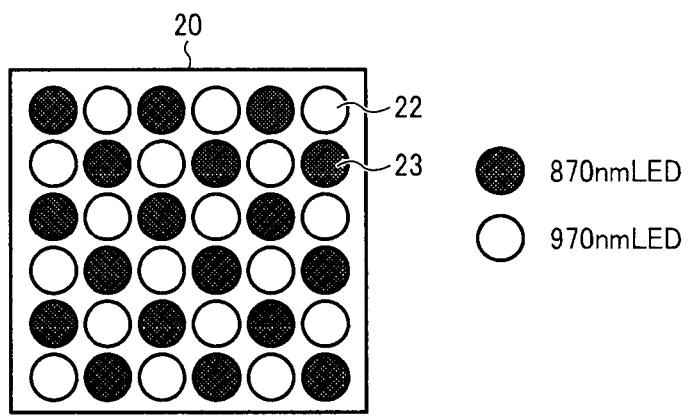
FIG. 3B
FIG. 4
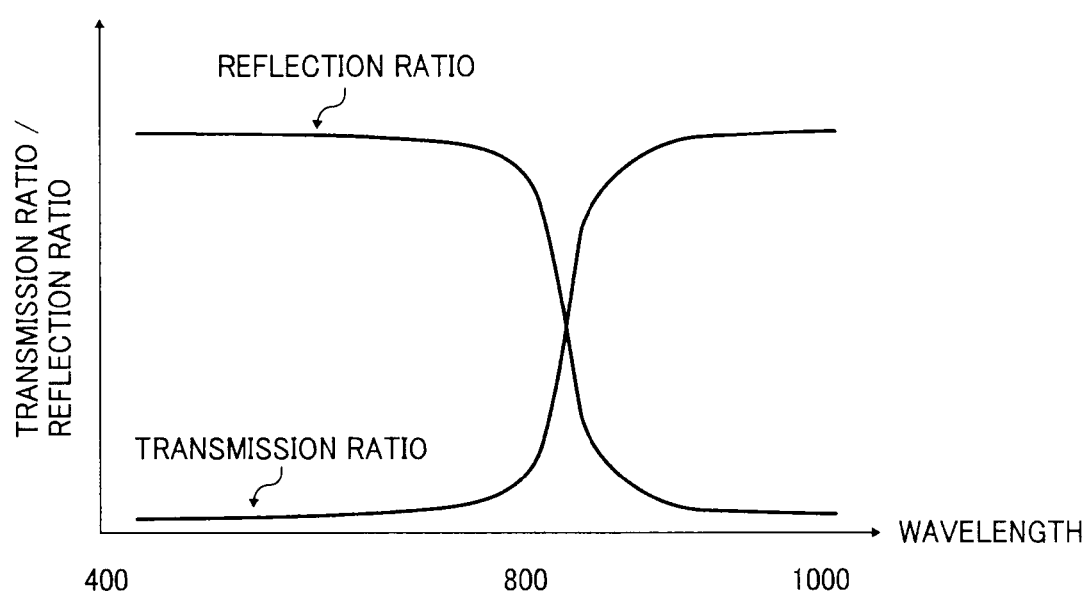

FIG. 6
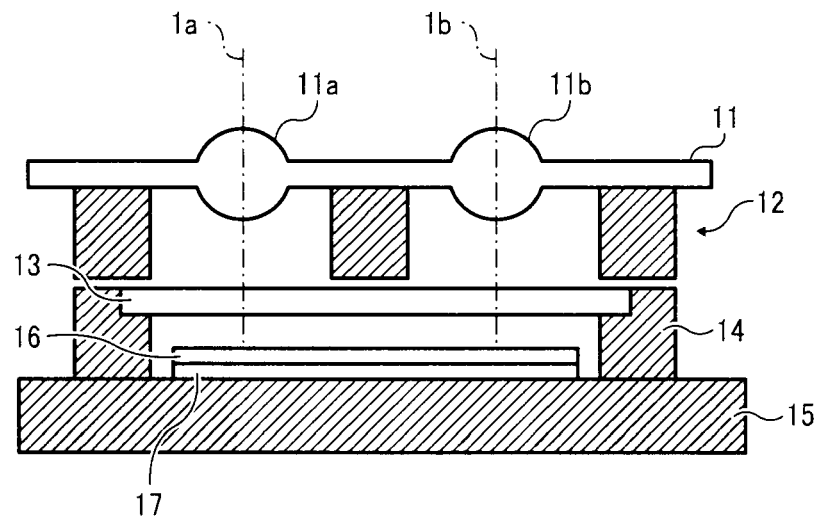
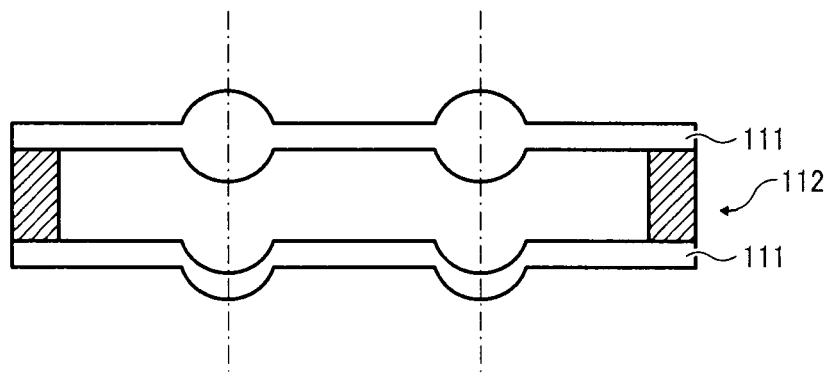
FIG. 7A
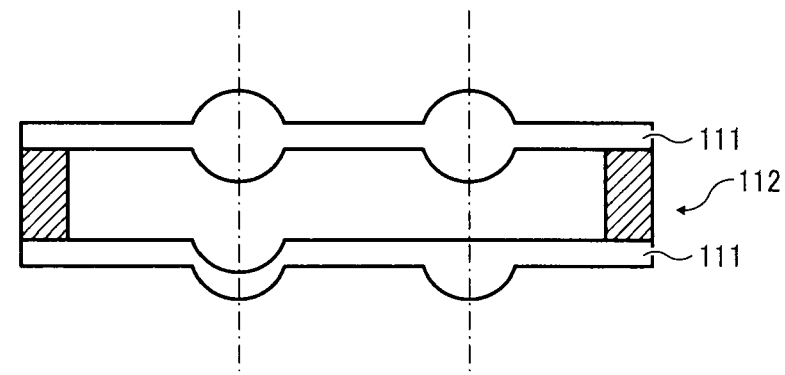
FIG. 7B

REFLOW METHOD

ION DIFFUSION METHOD

INKJET METHOD

GRAY SCALE MASK METHOD

IMAGE PICKUP

BACKGROUND OF THE INVENTION

1. Field of the Invention

The present invention relates to an image pickup, and more particularly to an image pickup for use in the detection of the driving status of a driver, etc.

2. Discussion of the Background

In recent years, detecting and monitoring the driving status of a driver all the time has been studied related to the drive assist system. In general, a method of taking a face image of a driver by an image pickup camera built in a rear view mirror (hereinafter referred to as a rear view mirror built-in image pickup) is used to detect the status of the driver. Securely taking face images of a driver in a wide range of illuminance from day to night is necessary.

A rear view mirror built-in image pickup adopting a near infrared pulse light projection method is already present to securely take face images of a driver from a low illuminance during night to a high illuminance during daytime. In this rear view mirror built-in image pickup, a light emission unit in which LEDs emitting light having a wavelength of 850 nm are arranged, an image pickup unit of a charge-coupled camera (CCD), etc are built-in a rear view mirror. The rear view mirror built-in image pickup irradiates an object (driver) with beams of near infrared having a wavelength of 850 nm in a pulse manner during which the shutter of the CCD camera is open to receive a reflection light image. When taking an image of a driver, a near infrared bandpass filter mirror which transmits beams of near infrared and reflects optical light required for the driver is used to receive a reflection light image with the CCD camera formed by irradiating the driver with the beams of near infrared without a loss while not hindering the function of the rear view mirror. In this rear view mirror built-in image pickup, images of a driver are securely obtained by using near infrared.

The object of detecting and monitoring the status of a driver during driving is to detect and monitor deterioration of consciousness due to dozing off, inattentive driving, etc. The rear view mirror built-in image pickup described above shoots a face image of a driver, takes out (detects) the face area and eye area from the face image, and measures blinks and the direction of the line of sight. The rear view mirror built-in image pickup detects the degree of deterioration of consciousness from the change in the time of shutting eyes of blinking and inattentive view from the direction of the face and/or the eyeball.

As described above, taking out the face area and the eye area from the face image of a driver taken by an image pickup is necessary to detect the driving status of the driver. Thus, placing the position of those areas at a high speed with high precision is demanded. For example, precision is required such that when a dummy (mannequin) sits at wheel, the dummy's face is not detected as the face of man. The rear view mirror built-in image pickup can securely shoot face images of a driver in the environment in which the illuminance changes from day to night. However, since the rear view mirror built-in image pickup employs a method of using only near infrared light having a single wavelength of 850 nm, placing the position of the face of a driver is limiting with regard to high precision.

In addition, another device, i.e., a near infrared multi-band image pickup, exists and uses near infrared light having a wavelength of 870 nm and near infrared having a wavelength of 970 nm. The near infrared multi-band image pickup irradiates the driver with near infrared having a wavelength of 870 nm and near infrared having a wavelength of 970 nm sequentially to obtain two images of 870 nm and 970 nm by a CCD camera. The image pickup detects the skin and hair portions by calculating the difference between the luminance values of the two irradiation images and discriminates the two portions from the symbol of the difference. The optical light is cut by an optical filter so that a secure image can be obtained.

The near infrared multi-band image pickup makes it possible to place the face of man with high accuracy but since the infrared having a wavelength of 870 nm and the infrared having a wavelength of 970 nm are emitted sequentially, images should be obtained by sequential lighting in a synchronized manner, which causes problems with regard to complexity and real time property.

SUMMARY OF THE INVENTION

Because of these reasons, the present inventor recognizes that a need exists for an image pickup which detects the driving status of a driver by placing the face portion of the driver with high precision and taking a face image in a real time manner.

Accordingly, an object of the present invention is to provide an image pickup which detects the driving status of a driver by placing the face portion of the driver with high precision and taking a face image in a real time manner.

Briefly this object and other objects of the present invention as hereinafter described will become more readily apparent and can be attained, either individually or in combination thereof, by an image pickup including a light emission portion that irradiates an object with near infrared; and an image pickup portion that receives a reflection light image of the object by the near infrared. The image pickup portion includes a lens array containing a substrate on which multiple lenses to respectively receive the reflection light image of the object by the near infrared are arranged; a light shield spacer that shields beams of light that have passed through the lens array from each other; a color filter separated into areas according to beams of light that pass through the light shield spacer, each of which transmits only particular beams of near infrared depending on the wavelengths thereof; and an image pickup element that simultaneously obtains multiple images of the object which are formed of each of the particular beams of near infrared having independent wavelengths that have passed through each of the areas of the color filter.

It is preferred that, in the image pickup mentioned above, the color filter is a laminate structure in which, in an XYZ orthogonal coordinate system, at least two kinds of transparent materials are alternately arranged in the Z direction on a substrate arranged in parallel with the XY plane, each layer of the laminate structure has one dimensional periodic concavo-convex form repeated in one direction in the XY plane determined depending on each of the areas and the beams of light that pass through the light shield spacer enters into the XY plane.

It is still further preferred that, in the image pickup mentioned above, the color filter has a groove or lattice structure arranged on a substrate with a regular cycle.

It is still further preferred that, in the image pickup mentioned above, the image pickup element is installed on an image pickup element holder, a spacer having a rectangle frame is provided on the image pickup element holder, the color filter is installed on the spacer, and the image pickup element is sealed by the spacer, the color filter, and the image pickup element holder.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein:

FIG. 3 is a diagram illustrating an example of the LED arrangement of the light emission portion;

FIG. 4 is a diagram illustrating the characteristics of the transmission ratio/reflection ratio of a near infrared bandpass filter;

FIG. 6 is a cross section illustrating the structure of the image pickup unit of the image pickup of the first embodiment of the present invention;

FIG. 7 is a diagram illustrating another example of the structure of the lens array for use in the present invention;

DETAILED DESCRIPTION OF THE INVENTION

The present invention will be described below in detail with reference to several embodiments and accompanying drawings. In the embodiments specified below, infrared having a wavelength of 870 nm and infrared having a wavelength of 970 nm are used in the near infrared multi-band image pickup described above. However, there is no specific limit to the number of the wavelengths. In general, higher precision processing is possible with a greater number of wavelengths.

Figure 1:
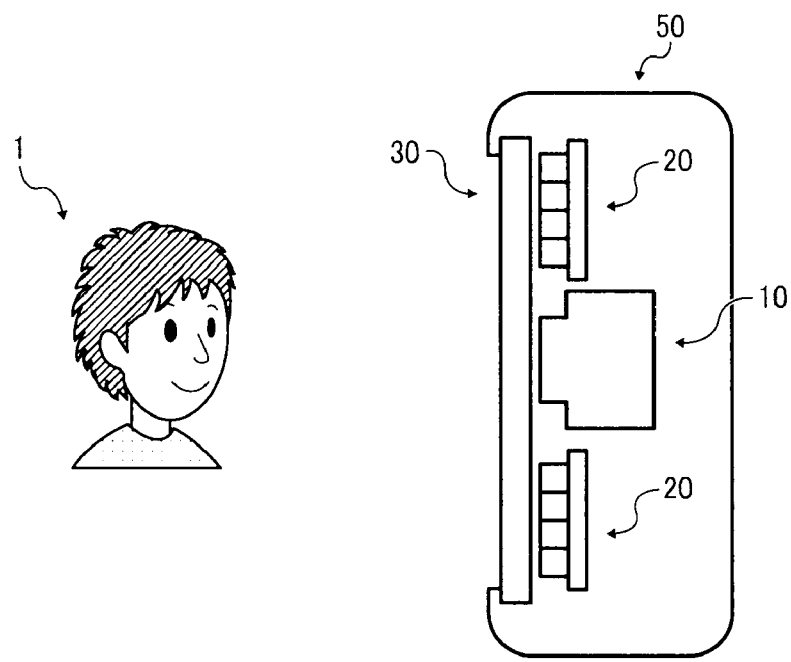
FIG. 1 is a diagram illustrating an example of the entire structure of the image pickup related to a first embodiment of the present invention.

FIG. 1 is a schematic diagram illustrating the entire structure of the image pickup related to a first embodiment of the present invention. In FIG. 1, a reference numeral 10 represents an image pickup unit such as a charge coupled device (CCD) that shoots a face image of a driver 1 as the object, and a reference numeral 20 represents a light emission unit that irradiates the driver 1 with near infrared using an infrared LED. The image pickup unit 10 and the light emission unit 20 are built in a rear view mirror 50 of a car to obtain the face image of the driver without being affected by the driving operation. A near infrared bandpass filter 30 is provided on the front of the rear view mirror 50. The near infrared bandpass filter 30 transmits emitted near infrared and reflects optical light so that the near infrared is projected to the driver 1 without a loss and the reflection light is received at the image pickup unit 10 while avoiding hindrance of the function of the rear view mirror 50 by taking images of the driver 1. In addition, a controller (not shown) which controls the shutter speed and the gain of the camera in the image pickup unit 10, and the emission timing of the infrared LED of the light emission unit 20 is built in the rear view mirror 50.

The light emission unit 20 emits near infrared in a pulse manner in synchronization with the image pickup timing determined by the controller (not shown). This near infrared passes through the near infrared bandpass filter 30 and is projected to the face portion of the driver 1. The reflection light passes through the near infrared bandpass filter 30 and is received on the image pickup unit 10 such as a CCD camera.

The image pickup unit 10 separates the received near infrared into two beams of light via a lens array employing a compound eye system and each beam of light enters into a color filter separated into different areas depending on the transmission wavelength of 870 nm or 970 nm and then into the image pickup element such as a CCD. Thus, two object (driver) images having different reflective characteristics reflecting the two wavelengths of 870 nm and 970 nm are obtained at the same time. A specific structure example of the image pickup 10 is described later.

Figure 2:
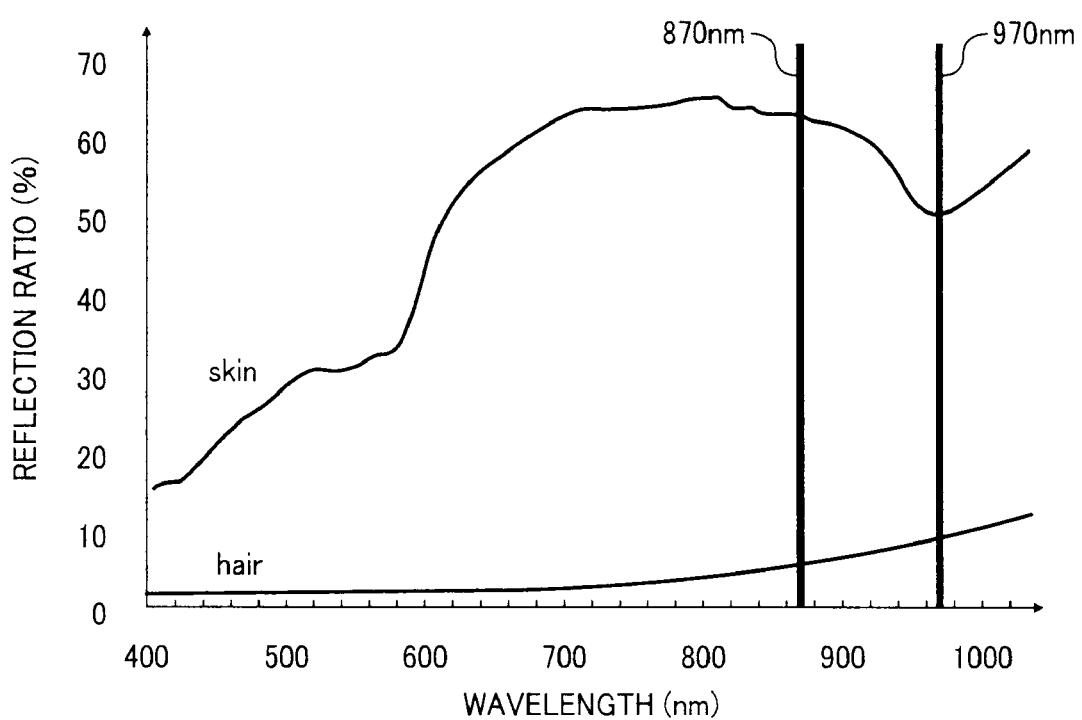
FIG. 2 is a diagram illustrating the characteristics of reflection characteristics in the near infrared range of the skin and hair of man.

Although invisible to a human being, a CCD camera can generally sense light beams having a wavelength of from 770 to 1,000 nm in the near infrared range. The reflection characteristics of the face portion of a man in the near infrared range are known as illustrated in FIG. 2. As in the case of the near infrared multi-band image pickup described above in the discussion of the background, when comparing the luminance values of the obtained two object images shot by using the selected two beams of light having wavelengths of 870 nm and 970 nm, the reflection characteristics of the skin and the hair are opposite, i.e., diagonally right down and right up, respectively. Therefore, when calculating the difference between the two object images, the symbols of the difference are opposite depending on the skin or the hair. Thus, the skin and the hair are discernable by the difference of the two object images shot by light beams having a wavelength of 870 nm and 970 nm.

After placing the skin portion, as in the case of the rear view mirror built-in image pickup described above in the discussion of the background, the face area and the eye area are detected followed by measuring blinking and the direction of the line of sight. The rear view mirror built-in image pickup detects the degree of deterioration of consciousness from the change in the time of shutting eyes due to blinking and inattentive view from the direction of the face and/or the eyeball. The rear view mirror built-in image pickup issues a caution to the driver 1 based on the obtained information.

The image pickup of this embodiment is improved in comparison with the near infrared multi-band image pickup described above in regards to the real time property because the two images having different reflection properties based on the two different wavelengths of 870 nm and 970 nm in the near infrared range are obtained at the same time. In addition, the image pickup of this embodiment is improved in comparison with the rear view mirror built-in image pickup described above in regards to the accuracy on placement of the face position of the driver 1 because the skin and hair portions are cut by calculating the difference between the luminance values of the two obtained image. Since the embodiment employs a near infrared pulse light projection method, the image pickup of the embodiment securely obtains an image in the environment from a low illuminance during night to a high illuminance during daytime as in the case of the rear view mirror built-in image pickup described above. Furthermore, since the image pickup of the embodiment is built in the rear view mirror 50 of a car, the face of the driver 1 is taken without being affected by the driving operation.

Structure examples of each unit of the image pickup of the present invention are described below with descriptions about the function, etc.

FIG. 3 is a diagram illustrating an example of the LED arrangement of the light emission unit. In the example illustrated in FIG. 3, the light emission unit 20 is structured by arranging multiple infrared LEDs around the image pickup unit 10 to cause the luminance of the image of the driver 1 to be uniform. FIG. 3A is a diagram illustrating an example in which multiple LEDs 21 that outputs near infrared in the wavelength range of from approximately 800 to 1,000 nm are uniformly arranged. FIG. 3B is a diagram illustrating an example in which infrared LEDs 22 and 23 emit beams of light having a single wavelength of 870 nm and 970 nm, respectively. Since LEDs have directionality, the LEDs 22 and 23 are arranged in a pattern illustrated in FIG. 3B to cancel un-uniformity of light. A diffusion board is optionally provided on the side of irradiation of the LEDs. The group of the infrared LEDs of FIG. 3A that output near infrared in the band of from approximately 800 to 1,000 nm or the group of the infrared LEDs of FIG. 3B that output a single wavelength of 870 nm or 970 nm is driven with a regular interval to irradiate the face portion of the driver 1 in a pulse manner via the near infrared bandpass filter 30 and the image pickup 10 receives the reflection light from the face portion only during this irradiation. As described later, the image pickup unit 10 separates this reflection light image and transmits the reflection light image through a color filter to obtain two images of two different reflection characteristics of two different wavelengths of 870 nm and 970 nm at the same time.

FIG. 4 is a diagram illustrating the characteristics of the transmission ratio to the reflection ratio of a near infrared bandpass filter. The near infrared bandpass filter 30 are required to transmit only the near infrared projected to the face of the driver 1 by the LEDs and reflect the optical light for the driver 1 and ambient light. Therefore, a filter having the characteristics of the transmission ratio to the reflection ratio as illustrated in FIG. 3 is used. Such a filter is easily manufactured by using photonic crystal, a sub-wavelength structure or a laminar structure in which each layer has a different refraction index.

Figure 5:
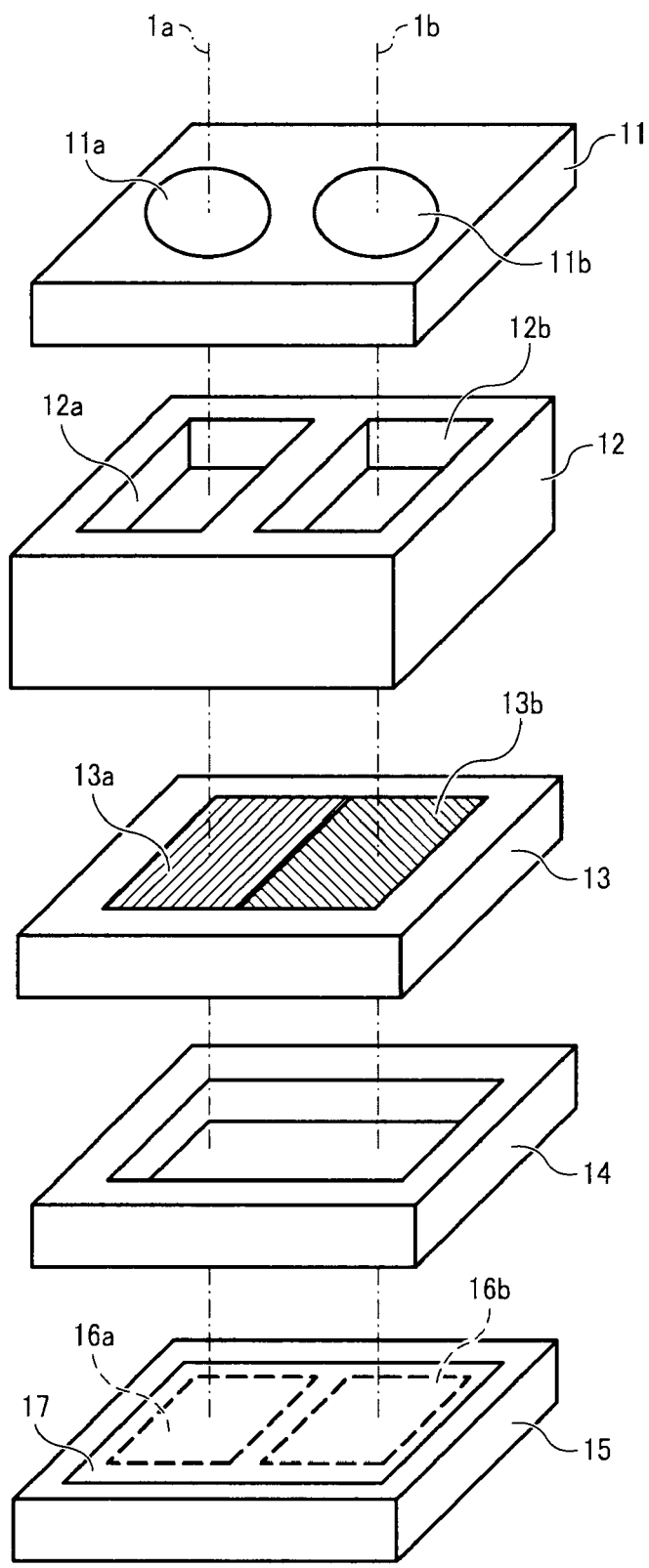
FIG. 5 is an exploded perspective view of the structure of the image pickup unit in the image pickup of the first embodiment of the present invention.

FIG. 5 is an exploded perspective view illustrating the structure of the image pickup unit in the image pickup of the embodiment illustrated in FIG. 1. FIG. 6 is a cross section illustrating the structure of the image pickup unit in the image pickup of the embodiment illustrated in FIG. 1. The image pickup unit 10 employs a compound eye system in which multiple lenses (two in this case) are used for one image pickup element. This compound eye system has an advantage in that the device is reduced in thickness.

In FIG. 5, the two lenses 11a and 11b are independent single lenses having the same form arranged on the same plane and form a lens array 11. Each of the optical axes 1a and 1b of the two lenses 11a and 11b is parallel to the normal line of the plane on which the two lenses 11a and 11b are arranged. The two single lenses 11a and 11b are formed of, for example, a nonspherical lens, etc.

As illustrated in FIG. 5, the direction in parallel with the optical axes 1a and 1b is defined to be Z axis, a direction perpendicular to the Z axis is defined to be X axis, and the direction perpendicular to the Z axis and the X axis is defined to be Y axis. The lenses 11a and 11b are situated on the lattice points formed of a straight line in parallel with the X axis and a straight line in parallel with the Y axis on the XY plane.

The light shield spacer 12 is provided on the opposite side of an object relative to the lens array 11. The light shield spacer 12 has openings (holes) 12a and 12b with the respective optical axes 1a and 1b as their centers. The openings 12a and 12b are empty holes (air layer) and the inside wall of the openings is treated (e.g., black-lacquered, roughened or matted) to prevent reflection of light, therefore, preventing stray light reflected at the inside wall from entering into the solid image pickup element, which is described later.

A color filter 13 on which color filter areas 13a and 13b are formed is arranged on the opposite side of the object relative to the light shield spacer 12. The color filter areas 13a and 13b are respectively provided in a plane parallel to the XY plane where the optical axes 1a and 1b pass. The color filter is an element which transmits only light beams having a particular wavelength. The color filter area 13a transmits near infrared having a wavelength of 870 nm and the color filter area 13b transmits near infrared having a wavelength of 970 nm.

An image pickup element holder 15 is provided via a spacer 14 on the opposite side of the object relative to the color filter 13. The image pickup holder 15 includes a substrate 17 having a digital signal processor (DSP) on which a solid image pickup element 16 such as a CCD is provided. The image pickup areas (areas on which the object is actually focused) of the solid image pickup element 16 are located on the same plane parallel to the XY plane. The optical axes 1a and 1b approximately pass through the corresponding centers of the two equally divided areas 16a and 16b (enclosed by dashes lines in this embodiment) of the image pickup area.

As illustrated in FIG. 6, the spacer 14 having a rectangle frame form is placed on the image pickup holder 15 and the color filter 13 is provided on the spacer 14. The image pickup areas 16a and 16b of the image pickup element 16 are sealed by the spacer 14, the color filter 13 and the image pickup holder 15 to prevent foreign material such as dust from entering into the image pickup areas 16a and 16b.

As described above, the image pickup unit 10 of this embodiment looks like a structure in which two image pickup units independently include a simple lens, a color filter, and an image pickup area on the two optical axes 1a and 1b. Different wavelength images are taken by each image pickup unit, which is described later.

As illustrated in FIG. 1, the near infrared that has passed through the near infrared bandpass filter 30 enters into each of the lenses 11a and 11b of the lens array 11 and then is independently concentrated into particular beams of light. Each beam of light after the lenses 11a and 11b is completely separated by the light shield spacer 12 and then enters into each color filter 13a and 13b of the color filter 13. The color filter area 13a transmits only near infrared having a wavelength of 970 nm and the color filter area 13b transmits only near infrared having a wavelength of 970 nm. The beams of light that have passed through the color filter area 13a of the color filter 13 are received on the area 16a of the solid image pickup element 16 and the beams of light that have passed through the color filter area 13b are received on the area 16b of the solid image pickup element 16. That is, two object images (face images of a driver) having different reflection properties based on the wavelengths of 870 nm and 970 nm are obtained by the solid image pickup element 16 at the same time.

In FIGS. 5 and 6, the lens array 11 is structured by an array of simple lenses. Also, a structure illustrated in FIG. 7A is suitable in which multiple lens arrays 111 are accumulated via a spacer 112. The form of each lens is made simple by increasing the number of lenses, which resultantly makes manufacturing of each lens easy. In addition, the form of each lens can be changed as illustrated in FIG. 7B. For example, the iris is adjusted by changing the aperture of the lens since the amount of incident light varies depending on the wavelength.

A method of manufacturing a lens array is illustrated in FIG. 8. Refer to P13 to P20 of Ricoh Technical Report, No. 29, published in December 2003.

Figure 8A:
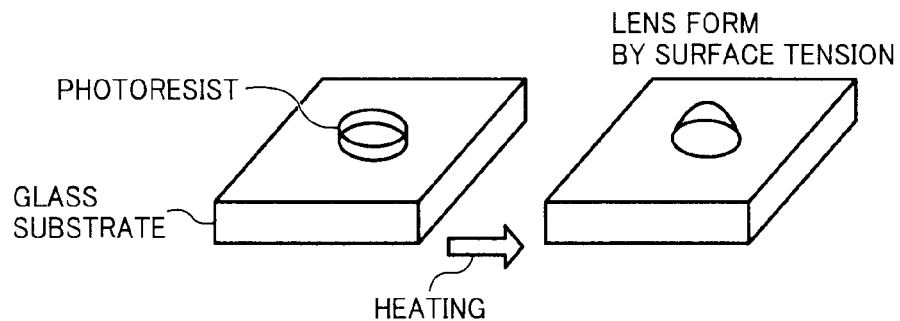
FIG. 8 is a diagram illustrating an example of the method of manufacturing the lens array for use in the present invention.
Figure 8B:
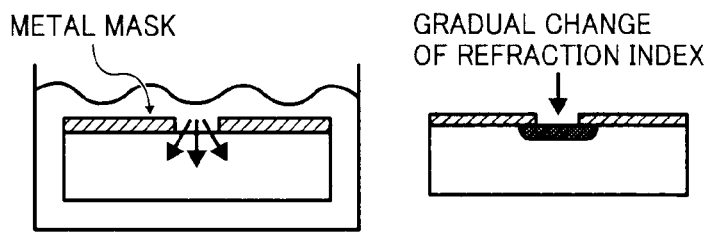
Figure 8C:
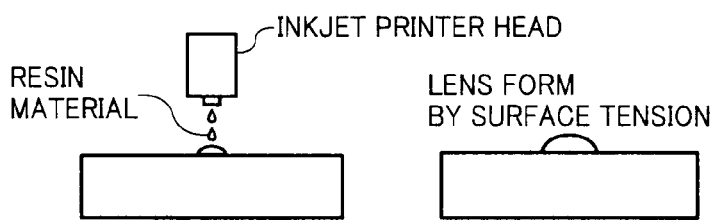

The reflow method illustrated in FIG. 8A is as follows: manufacture a photoresist pattern having a pillar form by photolithography on the surface of a glass substrate; heat the glass substrate to flow the photoresist; and form a lens form by the surface tension. The ion diffusion method illustrated in FIG. 8B is a method in which gradual changes in the refraction index are made on the glass substrate on which a mask to a lens form is formed by diffusing an ion such as $Tl^+$ in the glass substrate. The inkjet method illustrated in FIG. 8C is as follows: drop a tiny amount of resin material to a predetermined position using an inkjet printer head; and manufacture a lens form by the surface tension.

Figure 8D:
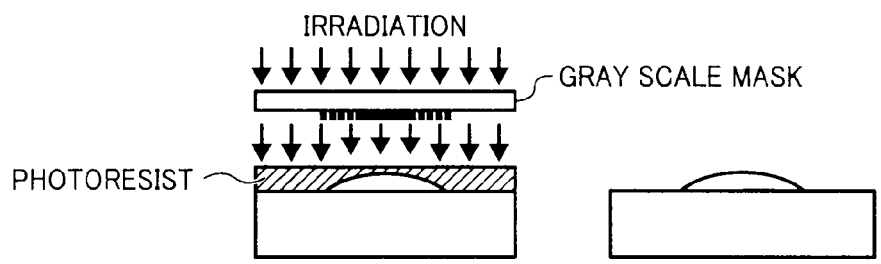

These methods use forms or refraction index distribution naturally created by the surface tension or ion diffusion as a lens. The gray scale mask method is illustrated in FIG. 8D. In this method, the photoresist form is controlled by the transmission ratio distribution provided to a gray scale mask. This method is relatively suitable to form various kinds of forms in comparison with the other methods. Thus, the gray scale method is increasingly important for the lens manufacturing technology in the future.

The reflow method and the gray scale method illustrated in FIG. 8 are illustrated until the lens form is formed by the photoresist. Generally, a lens manufactured by a photoresist has problems such that the lens manufactured as is has an insufficient transmission ratio and a weak resistance to humidity or exposure to light. Therefore, the resist pattern is transferred to a substrate material first by using an anisotropic dry etching. However, the resist form prepared by an anisotropic dry etching process may significantly different from the resist form before the etching. Thus, manufacturing a lens with a small error from the target form is difficult. In addition, this form change varies depending on the kind of used etching devices, the etching condition, and the kind of the material for a substrate. Particularly, the important factors such as the transmission ratio, the wavelength range, and the refraction index in terms of the evaluation on a lens are affected by the kind of the substrate. Therefore, making it possible to manufacture a lens having a high form precision from various kinds of substrate material is preferable.

In addition, a typical method of manufacturing a lens by grinding and a mold method of manufacturing a die and sealing a resin material into the die are also suitably used although these are not illustrated in figures.

Figure 9:
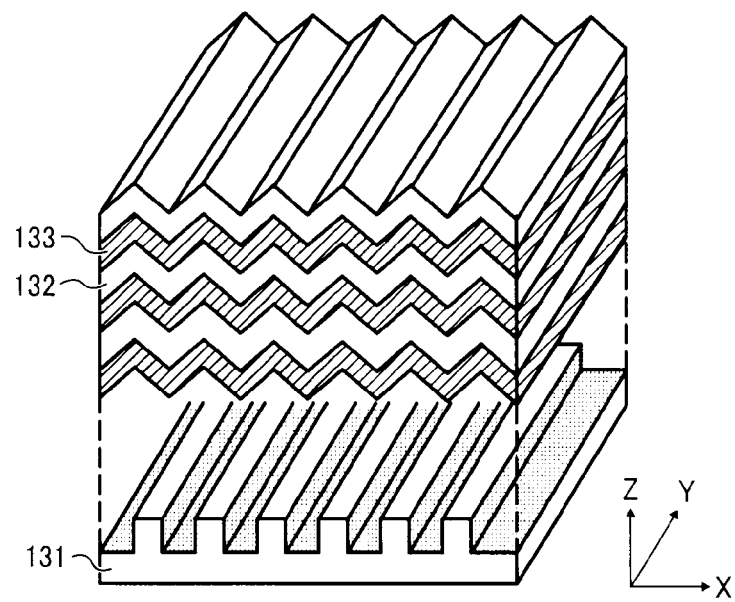
FIG. 9 is a diagram illustrating an example of the structure of the color filter for use in the present invention.

Next, the color filter is described. FIG. 9 is a conceptual diagram illustrating a color filter formed of photonic crystal. That is, a transparent medium 132 having a high fraction ratio and a medium 133 having a low fraction ratio are alternately accumulated while preserving the form of the interface therebetween. Each layer is of a periodicity in the X direction but can be uniform in the Y direction or have a periodic or non-periodic structure larger than the periodicity in the X direction. Such a fine periodic structure of photonic crystal can be manufactured with high reproducibility and uniformity by a system using a technology referred to as the self-cloning technology.

Figure 10:
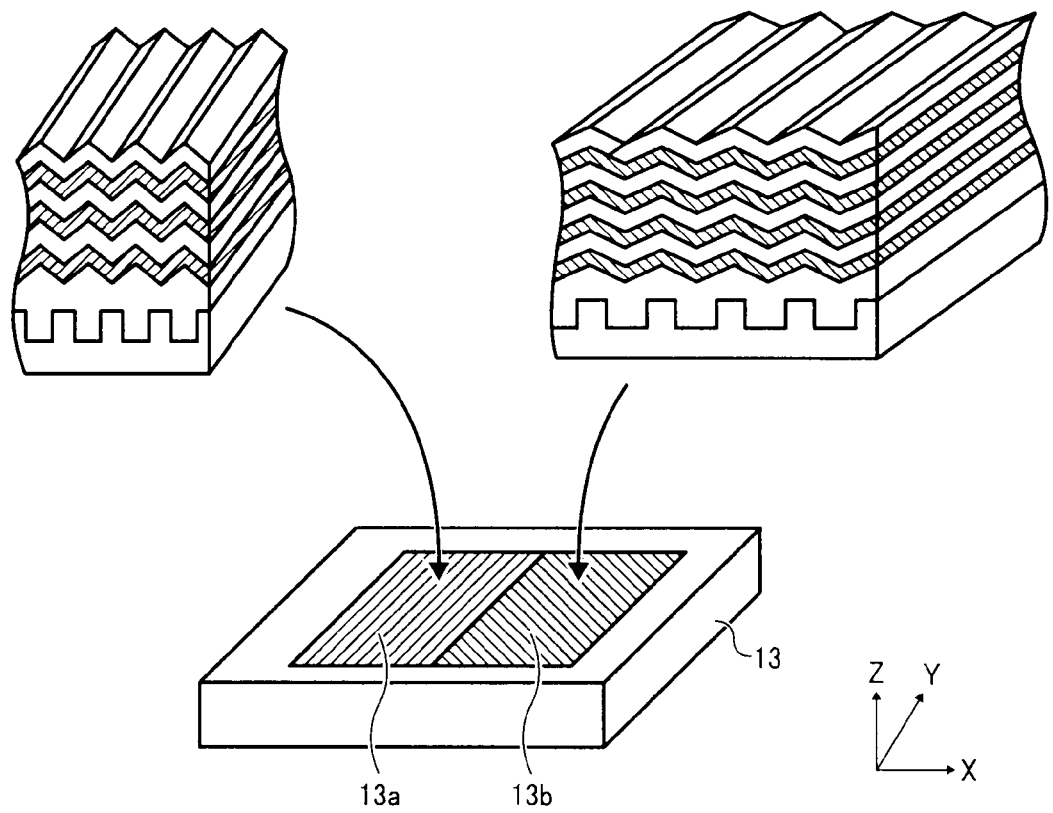
FIG. 10 is a diagram illustrating an example of the color filter of having the structure illustrated in FIG. 9.

FIG. 10 is a schematic diagram illustrating the color filter formed of two kinds of areas that transmit beams of light having different wavelengths. The color filter 13 has a structure illustrated in FIG. 9, which is a laminar structure, for example, including multiple alternate layers of $Ta_2O_5$ and $SiO_2$, having at least two kinds of transparent materials alternately accumulated along the Z direction on one substrate arranged in parallel with the XY plane in the orthogonal coordinate system. The color filter 13 is separated into two areas 13a and 13b in the XY plane in this embodiment and each area has a concavo-convex structure periodically repeated in one direction in the XY plane which is determined depending on each area.

When beams of light having two wavelengths ($\lambda 1$ and $\lambda 2$: $\lambda 1 < \lambda 2$) enter vertically into one of the main planes of the photonic crystal filter, signal beams of light having a particular wavelength are selectively output from the other one of the main planes.

The opening areas and the transmission axes of the color filter described above can be freely designed according to the size and/or direction of the groove patterns processed on a substrate first. The groove patterns are formed by various kinds of methods using, for example, electron beam lithography or photolithography, interference exposure, or nano-printing. In any method thereof, the groove direction can be determined for each area with high precision. Therefore, the color filter areas having a combination of fine color filters having different transmission axes, and a color filter having multiple color filter areas can be formed. In addition, only a particular area having a concavo-convex pattern can function as a color filter. Therefore, when the areas around the particular area are made to have a flat pattern or a concavo-convex pattern isotropic in the plane, light passes through the areas as media not having polarized wave dependency. Therefore, a color filter can be formed only on the particular area.

Figure 11A:
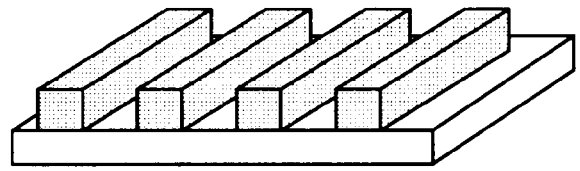
FIG. 11 is a diagram illustrating another example of the structure of the color filter for use in the present invention.
Figure 11B:
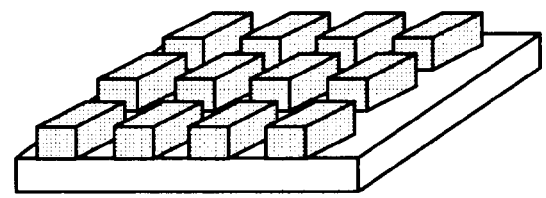

The color filter 13 is not limited to the photonic crystal type illustrated in FIG. 9. For example, a color filter having a sub-wavelength structure is suitably used. The color filter having a sub-wavelength structure has a periodic structure having a shorter cycle than the transmission wavelength. It is known that there is no diffraction wave other than zero dimensional light in a periodic structure having a cycle shorter than the wavelength of light and the optical characteristics of reflection light or transmission light significantly vary depending on the refraction index, thickness, form, etc. of material forming the lattice of the periodic stricture. FIG. 11A illustrates an example of the one dimensional sub-wavelength lattice and FIG. 11B illustrates a schematic diagram illustrating an example of the two dimensional sub-wavelength lattice. The optical characteristics such as reflection characteristics and transmission characteristics change in the one dimensional sub-wavelength lattice depending on the polarization of incident light but the polarization of incident light does not affect the optical characteristics in the two dimensional sub-wavelength lattice.

Figure 12A:
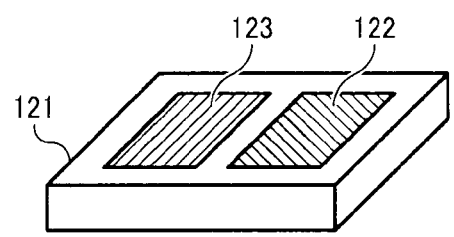
FIG. 12 is a diagram illustrating an example of the method of manufacturing the light shield for use in the present invention.
Figure 12B:
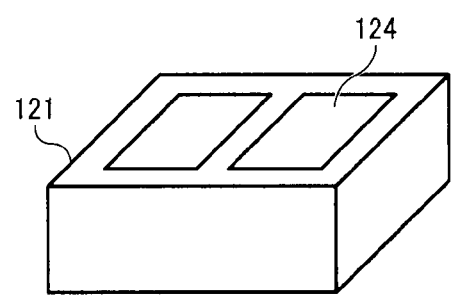
Figure 12C:
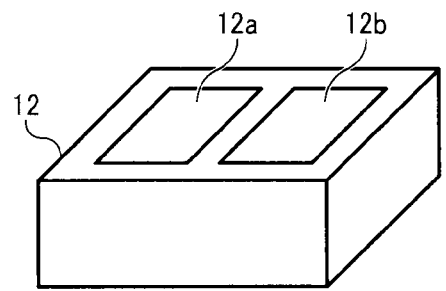

Next, the light shield spacer is described. FIG. 12 is a diagram illustrating a method of manufacturing a light shield spacer. As illustrated in FIG. 12A, a paint 122 that shields ultraviolet is applied to the outer surface of a sensitive glass 121 containing silver. The paint 122 is removed by patterning from a portion 123 where a shield wall is formed. After the sensitive glass 121 is irradiated with ultraviolet and the paint 122 is removed, silver precipitates and is blackened at the portion directly irradiated with the ultraviolet among the sensitive glass 121 to form a light shield wall 124. The light shield 124 is formed inside the sensitive glass 121. Finally, as illustrated in FIG. 12C, the sensitive glass 121 is subject to removal treatment such as mechanical processing or etching to form the light shield spacer 12 having the areas 12a and 12b corresponding to the color filter areas 13a and 13b.

According to the method illustrated in FIG. 12, the light shield spacer 12 is easily manufactured. In addition, the light shield spacer 12 easily prevents leak of light to the adjacent areas. Therefore, the light shield spacer 12 forms an image pickup unit having a compact size in the XY plane in combination with a lens array having multiple lenses arranged on the same plane.

The image pickup of the present invention is not limited to the structure having a lens array including two lenses with two color filter areas. Any structure having at least two areas for the lens array and the color filter is suitably used. For example, FIG. 13 illustrates a structure having 4 areas.

Figure 13:
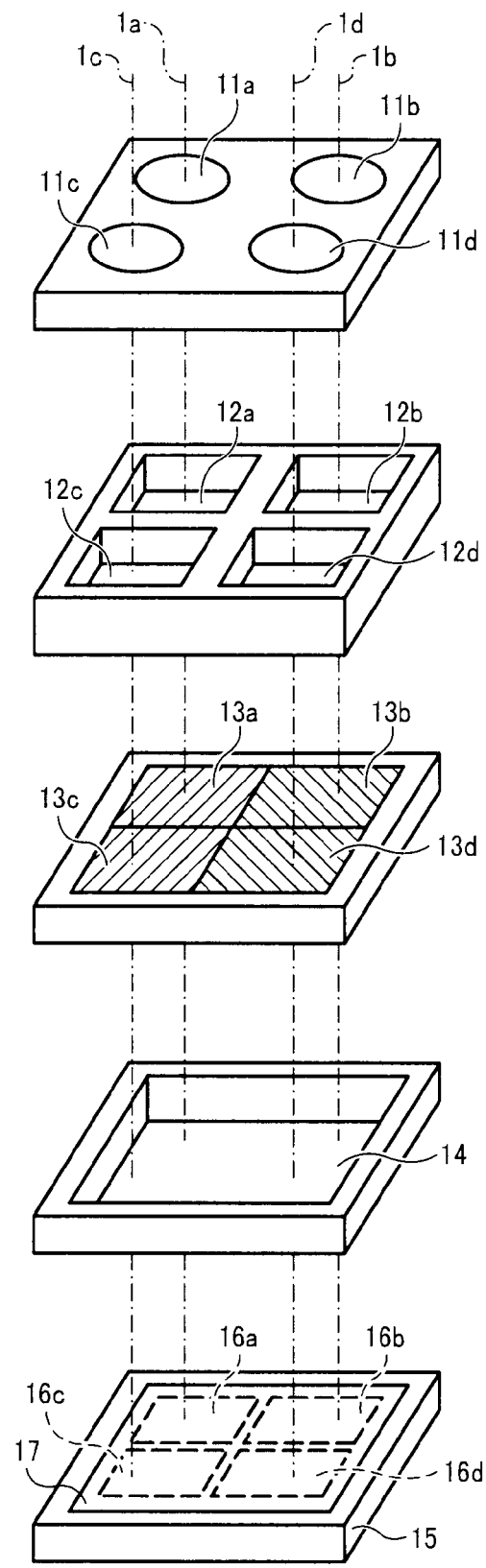
FIG. 13 is a diagram illustrating an example of the structure of the image pickup unit of the image pickup related to a second embodiment of the present invention.

FIG. 13 is an exploded perspective view illustrating a schematic structure of the image pickup unit in the image pickup of the second embodiment of the present invention. In FIG. 13, the two lenses 11a and 11b are independent simple lenses having the same form and arranged on the same plane to form the lens array 11. In addition, two lenses 11c and 11d are simple lenses having the same form but different from that of the two lenses 11a and 11b and are formed on the same plane as that for the two lenses 11a and 11b. Each axis of the four lenses 11a, 11b, 11c and 11d is parallel to the normal line of the plane on which the four lenses 11a, 11b, 11c and 11d are arranged. In this embodiment, the lenses 11a and 11b are formed to mainly obtain images of the driver 1 in a car and 11c and 11d are formed to mainly obtain images of a person sitting at the front passenger seat of the car.

As illustrated in FIG. 13, a parallel direction of the optical axes 1a, 1b, 1c and 1d is defined to be Z axis, a direction perpendicular to the Z axis is defined to be X axis and the perpendicular direction to the Z axis and X axis is defined to be Y axis. The lenses 11a and 11b are situated on the lattice points formed of a straight line in parallel with the X axis and a straight line in parallel with the Y axis on the XY plane.

The light shield spacer 12 is provided on the opposite side of an object relative to the lens array 11. The light shield spacer 12 has openings (holes) 12a, 12b, 12c and 12d with the respective optical axes 1a, 1b, 1c and 1d as their centers. The openings 12a, 12b, 12c and 12d are empty holes (air layer) and the inside wall of the openings is treated (e.g., black-lacquered, roughened or matted) to prevent reflection of light, thereby, preventing stray light reflected on the inside wall from entering into the solid image pickup element, which is described later.

A color filter 13 on which color filter areas 13a, 13b, 13c and 13d are formed is arranged on the opposite side of an object relative to the light shield spacer 12. The color filter areas 13a, 13b, 13c and 13d are respectively provided in a plane parallel to the XY plane where the optical axes 1a, 1b, 1c and 1d pass. The color filter is an element which transmits only light beams having a particular wavelength. The color filter areas 13a and 13b transmit near infrared having a wavelength of 870 nm and the color filter areas 13b and 13d transmit near infrared having a wavelength of 970 nm.

An image pickup element holder 15 is provided via a spacer 14 on the opposite side of the object relative to the color filter 13. The image pickup holder 15 includes a substrate having a digital signal processor (DSP) on which a solid image pickup element 16 such as a CCD is provided. The image pickup areas (areas on which the object is actually focused) of the solid image pickup element 16 are located on the same plane parallel to the XY plane. The optical axes 1a, 1b, 1c and 1d approximately pass through the corresponding centers of the four equally divided areas 16a, 16b, 16c and 16d (enclosed by dashes lines in this embodiment) of the image pickup area. Both images of the driver 1 and the front passenger in a car are optimally focused by employing a structure in which a lens array having lenses for the driver 1 and the front passenger is arranged. A processing unit having the same form as in the first embodiment is provided at the rear of each image pickup element to take images according to the wavelength information. Therefore, the image pickup having a more robust property to the image shooting position than that of the first embodiment is manufactured.

As an example of the image pickup of the present invention, the structure in which the image pickup of the present invention is built in a rear view mirror to shoot images of the driver is described above. The image pickup of the present invention is not limited thereto. The camera may be built in an instrument panel or can be arranged in combination with a head-up display. Furthermore, the image pickup of the present invention is not limited to the usage for a car but can be used for a factory (for factory automation) or in a healthcare medical field.

This document claims priority and contains subject matter related to Japanese Patent Applications Nos. 2008-159051 and 2009-013235, filed on Jun. 18, 2008, and Jan. 23, 2009, respectively, the entire contents of which are incorporated herein by reference.

Having now fully described the invention, it will be apparent to one of ordinary skill in the art that many changes and modifications can be made thereto without departing from the spirit and scope of the invention as set forth therein.

What is claimed as new and desired to be secured by Letters Patent of the United States is:

1. An image pickup comprising:
    a light emission portion configured to irradiate an object with near infrared; and
    an image pickup portion configured to receive a reflection light image of the object by the near infrared, the image pickup portion comprising:
        a lens array comprising a substrate on which multiple lenses to respectively receive the reflection light image of the object by the near infrared are arranged;
        a light shield spacer configured to shield beams of light that have passed through the lens array from each other;
        a color filter separated into areas according to beams of light that pass through the light shield spacer, each of the areas being configured to transmit only particular beams of near infrared depending on wavelengths thereof; and
        an image pickup element configured to simultaneously obtain multiple images of the object which are formed of each of the particular beams of near infrared having independent wavelengths that have passed through each of the areas of the color filter.

2. The image pickup according to claim 1, wherein the color filter is a laminate structure in which, in an XYZ orthogonal coordinate system, at least two kinds of transparent materials are alternately arranged in the Z direction on a substrate arranged in parallel with the XY plane, each layer of the laminate structure has one dimensional periodic concavo-convex form repeated in one direction in the XY plane determined depending on each of the areas and the beams of light that pass through the light shield spacer enters into the XY plane.

3. The image pickup according to claim 1, wherein the color filter has a groove or lattice structure arranged on a substrate with a regular cycle.

4. The image pickup according to claim 1, wherein the image pickup element is installed on an image pickup element holder, a spacer having a rectangle frame is provided on the image pickup element holder, the color filter is installed on the spacer, and the image pickup element is sealed by the spacer, the color filter, and the image pickup element holder.

5. The image pickup according to claim 1, wherein
a first area of the color filter transmits a particular beam having a first wavelength,
a second area of the color filter transmits a particular beam having a second wavelength, and
the first and second wavelengths are different.

6. The image pickup according to claim 5, wherein the image pickup element is configured to simultaneously obtain a first image having reflection properties of the first wavelength and a second image having reflection properties of the second wavelength.

7. The image pickup according to claim 5, further comprising a processor configured to
determine a first luminance value of a first image of the object obtained by the image pickup element and corresponding to the particular beam having the first wavelength that is transmitted by the first area of the color filter,
determine a second luminance value of a second image of the object obtained by the image pickup element and corresponding to the particular beam having the second wavelength that is transmitted by the second area of the color filter, and
determine a position of the object by comparing the first luminance value and the second luminance value, wherein
the first image of the object and the second image of the object are obtained during a same time period.

8. The image pickup according to claim 1, wherein
the lens array includes at least two lenses that each pass a beam of light, and
both beams of light passed by the two lenses of the lens array enter the color filter.

9. The image pickup according to claim 1, wherein the light shield spacer is configured to shield beams of light that have passed through each of the multiple lenses of the lens array from each other.

10. The image pickup apparatus according to claim 9, wherein the separated beams of light shielded from each other by the light spacer each pass to a different one of the separated areas of the color filter.

11. The image pickup according to claim 1, wherein the areas of the color filter are separated to correspond with the multiple lenses of the lens array.

12. The image pickup according to claim 1, wherein the light emission portion is configured to irradiate the object with near infrared having a wavelength between 800 and 1,000 nm.

13. The image pickup according to claim 12, wherein the areas of the color filter include a first color filter area which transmits near infrared having a wavelength of 870 nm and a second color filter area which transmits near infrared having a wavelength of 970 nm.

14. The image pickup according to claim 12, wherein the light emission portion includes an array of light emitting diodes (LEDs), each of the LEDs emitting near infrared having a wavelength between 800 and 1,000 nm.

15. The image pickup according to claim 12, wherein:
the light emission portion includes an array of first and second light emitting diodes (LEDs),
the first LEDs emit a single wavelength of 870 nm, and
the second LEDs emit a single wavelength of 970 nm.

16. The image pickup according to claim 15, wherein the first and second LEDs are arranged in an alternating pattern to cancel un-uniformity of light.

17. The image pickup according to claim 16, wherein the first and second LEDs are arranged in a checkered pattern to cancel un-uniformity of light.

* * * * *